US012156937B2

(12) United States Patent
Paiement et al.

(10) Patent No.: US 12,156,937 B2
(45) Date of Patent: *Dec. 3, 2024

(54) ORAL FILM FORMULATION FOR MODULATING ABSORPTION PROFILE

(71) Applicant: INTELGENX CORP., St-Laurent (CA)

(72) Inventors: Nadine Paiement, St-Laurent (CA); Rodolphe Obeid, St-Laurent (CA); Justin Conway, Carignan (CA); Billal Tir, Montréal (CA)

(73) Assignee: INTELGENX CORP., Saint-Laurent (CA)

( * ) Notice: Subject to any disclaimer, the term of this patent is extended or adjusted under 35 U.S.C. 154(b) by 0 days.

This patent is subject to a terminal disclaimer.

(21) Appl. No.: 17/952,300

(22) Filed: Sep. 25, 2022

(65) Prior Publication Data

US 2023/0047314 A1 Feb. 16, 2023

Related U.S. Application Data

(63) Continuation of application No. 17/063,644, filed on Oct. 5, 2020, now Pat. No. 11,471,406, which is a continuation of application No. 16/146,516, filed on Sep. 28, 2018, now Pat. No. 10,828,254.

(51) Int. Cl.
*A61K 9/00* (2006.01)
*A61K 31/4985* (2006.01)
*A61K 47/38* (2006.01)

(52) U.S. Cl.
CPC .......... *A61K 9/006* (2013.01); *A61K 31/4985* (2013.01); *A61K 47/38* (2013.01)

(58) Field of Classification Search
None
See application file for complete search history.

(56) References Cited

U.S. PATENT DOCUMENTS

| | | | |
|---|---|---|---|
| 4,695,463 A | 9/1987 | Yang et al. |
| 6,660,292 B2 | 12/2003 | Zerbe et al. |
| 7,132,113 B2 | 11/2006 | Zerbe et al. |
| 7,674,479 B2 | 3/2010 | Zerbe et al. |
| 7,824,588 B2 | 11/2010 | Yang et al. |
| 8,575,194 B1 | 11/2013 | Schultz |
| 8,642,080 B2 | 2/2014 | Bender et al. |
| 8,691,272 B2 | 4/2014 | Zerbe et al. |
| 8,703,191 B2 | 4/2014 | Zerbe et al. |
| 8,735,374 B2 | 5/2014 | Zerbe et al. |
| 9,149,472 B2 | 10/2015 | Schultz |
| 9,301,948 B2 | 4/2016 | Zerbe et al. |
| 9,539,334 B2 | 1/2017 | Wood et al. |
| 9,668,970 B2 | 6/2017 | Obeid et al. |
| 9,717,682 B2 | 8/2017 | Zerbe et al. |
| 9,833,461 B2 | 12/2017 | Modi |
| 9,949,934 B1 | 4/2018 | Zerbe et al. |
| 10,272,038 B2 | 4/2019 | Obeid et al. |
| 10,406,186 B2 | 9/2019 | Finley et al. |
| 10,603,301 B2 | 3/2020 | Sinai et al. |
| 10,610,528 B2 | 4/2020 | Zerbe et al. |
| 10,722,476 B2 | 7/2020 | Zerbe et al. |
| 10,828,254 B2 | 11/2020 | Paiement et al. |
| 10,940,173 B2 | 3/2021 | Finley et al. |
| 11,033,493 B2 | 6/2021 | Obeid et al. |
| 11,471,406 B2 | 10/2022 | Paiement et al. |
| 11,602,504 B2 | 3/2023 | Madwar et al. |
| 11,648,212 B2 | 5/2023 | Bilal et al. |
| 2001/0007680 A1 | 7/2001 | Kolter et al. |
| 2004/0131661 A1 | 7/2004 | Auffret |
| 2004/0156794 A1 | 8/2004 | Barkalow et al. |
| 2005/0107426 A1 | 5/2005 | Overeem et al. |
| 2007/0053939 A1 | 3/2007 | Yokoyama |
| 2007/0190139 A1 | 8/2007 | Zerbe et al. |
| 2007/0281003 A1 | 12/2007 | Fuisz et al. |
| 2008/0057112 A1 | 3/2008 | Knoop et al. |
| 2009/0098211 A1 | 4/2009 | Zalit et al. |
| 2009/0214640 A1 | 8/2009 | Szabo et al. |
| 2010/0297232 A1 | 11/2010 | Myers et al. |
| 2011/0136815 A1 | 6/2011 | Zerbe et al. |
| 2011/0142889 A1 | 6/2011 | Lee et al. |
| 2011/0263606 A1 | 10/2011 | Zerbe et al. |
| 2011/0305768 A1 | 12/2011 | Mao et al. |
| 2012/0141585 A1 | 6/2012 | Coulter |
| 2012/0156229 A1 | 6/2012 | Park et al. |
| 2013/0039932 A1 | 2/2013 | Park et al. |
| 2013/0177605 A1 | 7/2013 | Asari et al. |
| 2014/0065217 A1 | 3/2014 | Zerbe et al. |

(Continued)

FOREIGN PATENT DOCUMENTS

| | | |
|---|---|---|
| CA | 2489106 | 12/2003 |
| CA | 2535803 | 3/2005 |

(Continued)

OTHER PUBLICATIONS

The Dow Chemical Company, 2002 (Year: 2002).*
López-Olaondo et al (British Journal of Anaesthesia, 1996, 76, 835-840). (Year: 1996).*
"Gum arabic", From Wikipedia, the free encyclopedia. [online] Retrieved from "http://en.wikipedia.org/w/index.php?title=Gum_arabic&oldid=767071650". Feb. 23, 2017.
Morepen, The Joy of Growing Together, [online] Retrieved from "http://www.morepen.com/api-product-information.htm". (2010). (The year of publication is sufficiently earlier than the effective U.S. filing date so that the particular month of publication is not an issue).
Okumu et al., "Dynamic Dissolution Testing to Establish In Vitro/In Vivo Correlations for Montelukast Sodium, a Poorly Soluble Drug", Pharmaceutical Reasearch, vol. 25, No. 12, Dec. 2008.

(Continued)

*Primary Examiner* — Celeste A Roney
(74) *Attorney, Agent, or Firm* — Smart & Biggar LP

(57) ABSTRACT

An oral film dosage form includes a high viscosity polymer in an amount of from 1% to 5% by dry weight to reduce, modulate and/or control Cmax of an active agent. The high viscosity polymer has a viscosity of from 100 cps to 500 cps as determined at 2% concentration in water by weight at 25° C. using a Brookfield LVF viscometer with spindle no. 2 at 60 rpm.

20 Claims, 4 Drawing Sheets

(56) References Cited

U.S. PATENT DOCUMENTS

| | | | |
|---|---|---|---|
| 2014/0155483 A1 | 6/2014 | Li et al. | |
| 2015/0265720 A1 | 9/2015 | Levine et al. | |
| 2016/0015683 A1 | 1/2016 | McCarty | |
| 2016/0022595 A1 | 1/2016 | Shikani et al. | |
| 2016/0051510 A1 | 2/2016 | Allen et al. | |
| 2016/0074396 A1* | 3/2016 | Jeon | A61K 47/32 |
| | | | 514/250 |
| 2016/0173245 A1 | 6/2016 | Brewer | |
| 2016/0220480 A1 | 8/2016 | Bilal et al. | |
| 2016/0228385 A1 | 8/2016 | Sievers et al. | |
| 2016/0229845 A1 | 8/2016 | Cao et al. | |
| 2016/0243036 A1 | 8/2016 | Paiement et al. | |
| 2016/0324773 A1 | 11/2016 | Paiement et al. | |
| 2016/0346339 A1 | 12/2016 | Finley et al. | |
| 2017/0143623 A1 | 5/2017 | Cilurzo et al. | |
| 2017/0216220 A1 | 8/2017 | Bilal et al. | |
| 2017/0246120 A9 | 8/2017 | Stepovich | |
| 2017/0252300 A1 | 9/2017 | Modi | |
| 2017/0258710 A1 | 9/2017 | Conway et al. | |
| 2017/0290807 A1* | 10/2017 | Mundada | A61K 47/36 |
| 2017/0290870 A1 | 10/2017 | Schaneville | |
| 2017/0304319 A1* | 10/2017 | Westrin | A61P 1/08 |
| 2017/0333387 A1 | 11/2017 | Sarne | |
| 2018/0042890 A1 | 2/2018 | Sinai et al. | |
| 2018/0078549 A1 | 3/2018 | Zerbe et al. | |
| 2018/0110724 A1 | 4/2018 | Zerbe et al. | |
| 2018/0250240 A1 | 9/2018 | Paiement et al. | |
| 2018/0289665 A1 | 10/2018 | Turner et al. | |
| 2018/0303791 A1 | 10/2018 | Sinai et al. | |
| 2019/0060381 A1 | 2/2019 | Ballan et al. | |
| 2019/0133925 A1 | 5/2019 | Paiement et al. | |
| 2019/0209459 A1 | 7/2019 | Obeid et al. | |
| 2019/0231685 A1 | 8/2019 | Paiement et al. | |
| 2019/0247505 A1 | 8/2019 | Paiement et al. | |
| 2019/0290595 A1 | 9/2019 | Zerbe et al. | |
| 2019/0314293 A1 | 10/2019 | Bilal et al. | |
| 2019/0314326 A1 | 10/2019 | Garti et al. | |
| 2020/0054701 A1 | 2/2020 | Finley et al. | |
| 2020/0093786 A1 | 3/2020 | Sinai et al. | |
| 2020/0138730 A1 | 5/2020 | Madwar et al. | |
| 2020/0138885 A1 | 5/2020 | Paiement et al. | |
| 2020/0188348 A1 | 6/2020 | Sinai et al. | |
| 2020/0215063 A1 | 7/2020 | Zerbe et al. | |
| 2020/0268817 A1 | 8/2020 | Ballan et al. | |
| 2021/0015738 A1 | 1/2021 | LaRossa et al. | |
| 2021/0036310 A1 | 2/2021 | Hou et al. | |
| 2021/0316347 A1 | 10/2021 | Klöckner | |
| 2021/0393611 A1 | 12/2021 | Madwar et al. | |
| 2022/0008381 A1 | 1/2022 | Garti et al. | |
| 2022/0031781 A1 | 2/2022 | Finley et al. | |
| 2022/0362164 A1 | 11/2022 | Paiement et al. | |
| 2022/0395452 A1 | 12/2022 | Paiement et al. | |
| 2022/0409584 A1 | 12/2022 | Bilal et al. | |
| 2023/0201130 A1 | 6/2023 | Madwar et al. | |
| 2023/0225965 A1 | 7/2023 | Tir et al. | |
| 2023/0248660 A1 | 8/2023 | Bilal et al. | |

FOREIGN PATENT DOCUMENTS

| | | |
|---|---|---|
| CA | 2910206 | 12/2015 |
| CA | 2922959 | 6/2016 |
| CA | 3017264 | 9/2017 |
| CA | 3020798 | 10/2017 |
| CA | 2998218 | 4/2018 |
| CA | 9044248 | 5/2018 |
| CA | 3056944 | 10/2018 |
| CA | 3067822 | 12/2018 |
| CA | 3017526 A1 | 3/2020 |
| CN | 106176685 A | 12/2016 |
| EP | 0743064 A1 | 11/1996 |
| WO | 9940898 | 8/1999 |
| WO | 2005120256 | 12/2005 |
| WO | 2007052121 | 5/2007 |
| WO | 2008038155 A2 | 4/2008 |
| WO | 2012121461 A1 | 9/2012 |
| WO | 2013107810 A1 | 7/2013 |
| WO | 2016134454 A1 | 9/2016 |
| WO | 2018176149 A1 | 10/2018 |
| WO | 2018205017 A1 | 11/2018 |
| WO | 2020051709 A1 | 3/2020 |
| WO | 2022165607 A1 | 8/2022 |
| WO | 2022170442 A1 | 8/2022 |

OTHER PUBLICATIONS

Raghavendra Rao N. G et al., "Development of Mucoadhesive Films for Buccal Administration of Montelukast", IJPT, Mar. 2010, vol. 2, Issue No. 1, 1-15.

Bala et al., "Orally dissolving strips: A new approach to oral drug delivery system", Int. Journal Investig. Apr.-Jun. 2013; 3(2): 67-76.

Carrier oil and dosing, 2016 (Year: 2016). (The year of publication is sufficiently earlier than the effective U.S. filing date so that the particular month of publication is not an issue).

Venkateswarlu et al., "Preparation and Evaluation of Fast Dissolving Buccal Thin Films of Bufotenin", iMedPub Journals (Dec. 5, 2016), vol. 2, No. 4:12.

Hallucinogens: LSD, Peyote, Psilocybin, and PCP. National Institute on Drug Abuse (2008).

Baliga, S. et al. "Salivary pH: A diagnostic biomarker". J Indian Soc Periodontol, 17(4) :461-465 (Jul.-Aug. 2013).

Khatoon, N. et al. "Formulation and evaluation of oral fast dissolving films of montelukast sodium". International Journal of Pharmaceutical Sciences and Research, 5: 1780-1787 (May 2014).

Hughes, L. "Ion exchange resinates—the technology behind the mystery" 2005, Pharmaceutical Technology Europe, 17 (4), 38-42.

Balakrishnan, P., et al. Enhanced oral bioavailability of Coenzyme Q10 by self-emulsifying drug delivery systems. International Journal of Pharmaceutics, (2009), 374(1-2), 66-72.

Eleftheriadis, Georgios K. et al. Unidirectional drug release from 3D printed mucoadhesive buccal films using FDM technology: In vitro and ex vivo evaluation. European Journal of Pharmaceutics and Biopharmaceutics 144 (2019) 180-192.

Vieira, E. et al., Evaluation of Brewer's spent yeast to produce flavor enhancer nucleotides: influence of serial repitching. Aug. 20, 2013, Journal of Agricultural and Food Chemistry, vol. 61, 8724-8729.

English Translation of WO2012121461A1, published Sep. 13, 2012. Machine Translation.

Vishvakarma, "Design and development of montelukast sodium fast dissolving films for better therapeutic efficacy", Journal of the Chilean Chemical Society, 63(2), pp. 3988-3993, Jun. 1, 2018 (Jun. 1, 2018).

* cited by examiner

ORAL FILM FORMULATION FOR MODULATING ABSORPTION PROFILE

CROSS-REFERENCE TO RELATED APPLICATIONS

The present application is a continuation application of U.S. patent application Ser. No. 17/063,644 filed on Oct. 5, 2020, that is a continuation application of U.S. patent application Ser. No. 16/146,516 filed on Sep. 28, 2018. This document is hereby incorporated by reference in its entirety.

FIELD OF THE DISCLOSURE

This disclosure relates to oral film dosage formulations and processes for preparing oral film dosage forms, and more particularly to the preparation of oral film dosage forms that exhibit enhanced bioavailability.

BACKGROUND OF THE DISCLOSURE

It is often desirable to administer a pharmaceutical ingredient using an oral film dosage form. Oral film dosage forms have several advantages when compared with tablet and capsules. Many people have difficulty swallowing tablets and capsules, and risk choking while attempting to swallow solid oral dosage forms, but can self-administer a film dosage form without difficulty.

While administration of a drug in an oral film dosage form can be desirable, designing an oral dosage form that provides a desirable absorption profile remains a challenge. Oral film formulations have the potential to enhance the rate of absorption of drug or active pharmaceutical ingredient (API). However, faster absorption is sometimes undesired. For example, faster absorption can be undesirable when the target API bioavailability is to be maintained over an extended period of time or when a high $C_{max}$ (concentration maximum) should be avoided due to associated negative side effect or adverse events. A quick delivery of the API could also oversaturate the system and result in a portion of the API being lost. For instance, erectile dysfunction (ED) treatment sometimes requires ongoing treatment for a continuous period of several days if not weeks. The quick absorption followed by high $C_{max}$ of API administered orally via oral film creates a problem long solved by conventional tablets. Tablet capsules are routinely formulated with extended release technologies allowing modulation of the API release profile in the body thereby mitigating rapid oral absorption. Tablets and capsules are also routinely formulated to overcome poor solubility of the active agent. However, the techniques used for controlling API release and/or for overcoming poor API solubility with tablets or capsules are not well suited for solving similar problems with film oral dosage forms, which have additional constraints related to manufacturing of oral films with adequate mechanical and physical film properties.

The prior art fails to provide an adequate solution for the formulation of oral films or a method of formulating an oral film dosage form to reduce or modulate the $C_{max}$ observed from the in vivo absorption of the API. Further challenges associated with film strip technology include maintenance of API content uniformity and retaining a desired API structure or form. Yang (U.S. Pat. No. 7,824,588) discusses the various factors that could affect the final content uniformity of the film: formation of air pockets during mixing, improper casting, viscosity of the starting precursor solutions, improper drying methods (associated with long drying times), final water content of films, etc. These challenges escalate when API is poorly water soluble.

Poorly soluble particulate API can aggregate or grow if the film processing conditions are not favorable. U.S. Pat. Pub. No. 2011/0305768 discloses the preparation of quick dissolving films containing pH-sensitive micro particles encapsulated with bioactive agents. The pH-sensitive micro particles were prepared by a double emulsion solvent evaporation method. Though this method offers targeted release of protein-based compounds, it is a complicated and time-consuming process. Further, this method is not cost effective, and the final product may contain an unacceptable level of residual organic solvents.

Despite the successful development of rapidly dissolvable orally consumable films, there is still room for improvement in the speed with which the film dissolves in the mouth. Rapid dissolution of the film is desirable (e.g., within about 30-40 seconds) to reduce undissolved film residue that imparts an unacceptable, unpalatable, slimy feel to the palate of the consumer.

Fast dissolving films can provide an improved absorption profile of the active agent in vivo. However, a significant difficulty arising from the development of a fast dissolving oral film is the quick onset of the active agent could yield an unacceptably high $C_{max}$ shortly following administration of the film.

Pharmacokinetics refers to the movement of drugs into, though, and out of the body, as well as the time course of its absorption, bioavailability, distribution, metabolism, and excretion. An API $C_{max}$ is a standard measurement in pharmacokinetics related to drug absorption. $C_{max}$ represents the maximum (or peak) serum concentration that a drug reaches in a specified compartment or test area of the body after the drug has been administrated and before the administration of a second dose. $C_{min}$ is the minimum (or trough) concentration that a drug achieves between repeated dosing. $T_{max}$ is the time at which the $C_{max}$ is observed. After an intravenous administration, $C_{max}$ and $T_{max}$ are closely dependent on the rate of absorption and the experimental protocol, since the concentrations are always decreasing after the dose. After oral administration, $C_{max}$ and $T_{max}$ are dependent on the extent, and the rate of drug absorption. These values are used to compare the absorption profiles of different formulations of an API in the same subject. Short term drug side effects are most likely to occur at or near the $C_{max}$, whereas the therapeutic effect of drug with sustained duration of action usually occurs at concentrations slightly above the $C_{min}$ assuming minimum efficacy level is reached, that is the minimum efficacy level is below $C_{min}$. The $C_{max}$ is often measured in an effort to show bioequivalence (BE) between a generic and an innovator drug product. $C_{max}$ in combination with area under the curve (AUC) is also used to show BE in cases where a drug product is reformulated for administration through a different dosage form (for example when an injectable or tablet/capsule is replaced by an oral film). The FDA determines drug quality bioavailability (BA) and BE relying on pharmacokinetic measurements such as AUC and $C_{max}$ which are reflective of systemic exposure.

Attaining BE for an oral film dosage form from a tablet administered drug is generally hindered by a drug's high $C_{max}$ which as outlined above and is typically associated with the drug's side effects. High $C_{max}$ problems may be encountered when designing a generic formulation for a tablet. However, such high $C_{max}$ problems are even more prevalent in the formulation of oral film. Most methods for reducing the $C_{max}$ of a drug through extended release technology have been developed for tablet and capsule oral dosage forms, and are not generally adaptable to film dosage forms.

In addition to known problems with high $C_{max}$, film formulation is also affected by the poor water solubility of known drugs.

There is thus a need for an improved and/or alternative cost-effective oral film formulations and processes for making same to control the absorption of drugs, including poorly water soluble drugs, and mitigate the high early $C_{max}$ often associated with drugs side effects.

These and other inefficiencies and opportunities for improvement are addressed and/or at least partially overcome by the systems, assemblies and methods of the present disclosure.

SUMMARY OF THE DISCLOSURE

Disclosed is an oral film dosage form and process for extending the in vivo absorption of the API administered through oral film dosage form. The present disclosure relates to an oral film dosage for extending the release period of orally delivered API via oral film dosage form and methods of reducing, modulating, or controlling an oral film API's in vivo $C_{max}$.

According to some aspects of the disclosure, the oral dosage form delivers API which has a substantial component of enteral absorption.

The present disclosure relates to the use of very low level or percentage (weight/weight) of high viscosity polymer to control the in vivo absorption of an immediate release oral film.

The disclosed oral film dosage form comprises very low quantity, between 1-5%, of highly viscous polymer to unexpectedly significantly impact in vivo absorption of the active molecule or API.

It would generally be expected that a small presence of polymer will not impact absorption occurring later down in the gastrointestinal tract (GIT). In certain embodiments, an oral film dosage form uses Hydroxypropylcellulose (HPC) having particular characteristics for mitigating the quick onset and high $C_{max}$ of immediate release oral film dosage form following administration of the oral dosage, particularly for poorly water soluble API. The disclosed oral film formulation uses high viscosity polymers to reduce the early onset of immediate release oral films while potentially significantly extending the in vivo absorption and thus bioavailability of API.

In certain aspects of this disclosure, a formulation and process is disclosed to minimize the quick onset of drugs administered through immediate release oral film dosage form.

In certain aspects of this disclosure, a formulation is disclosed for administering tadalafil through oral film dosage form while maintaining an absorption profile within 20% of the profile of the commercial tadalafil brand tablet.

In certain aspects of this disclosure, the process for manufacturing oral film dosage forms has an in vivo extended release absorption profile.

In certain aspect of this disclosure, a process is disclosed for mitigating high early onset API absorption usually associated with quick dissolution of oral films. The process for mitigating high early onset uses low quantities of highly viscous polymers.

In certain aspects of this disclosure, the disclosed process comprises the addition of between about 1% and about 3% (weight/weight) of highly viscous polymers such as HPC to reduce the $C_{max}$ resulting from the early in vivo absorption of the API and potentially mitigating any side effects generally associated with such high early onsets.

In certain other aspects of this disclosure, the oral film for providing transport of an agent in a buccal cavity of a subject, comprises a dissolvable or disintegrable film matrix comprising HPC and an active agent. The oral film has at least a portion of the active agent destined for enteral absorption of the active agent. The HPC comprised in the oral film has a weight-average molecular weight determined by sized exclusion chromatography which is between about 200,000 and about 500,000 Dalton, preferably between about 300,000 to about 400,000 Dalton, more preferably about 325,000 to about 375,000 Dalton. The HPC is further characterized as having a viscosity of between about 100 to about 500 cps determined at 2% concentration in water by weight at 25° C. using a Brookfield LVF viscometer with spindle no. 2 at 60 rpm.

The HMWP/API weight ratios may vary depending on the active agent. The HMWP/API weight ratio is typically in the range of about typically 2:1 to 12:1, preferably 5:1 to 10:1, and more preferably 6:1 to 8:1.

These and other features, advantages and objects of the various embodiments will be better understood with reference to the following specification and claims.

DETAILED DESCRIPTION

Figure 1:
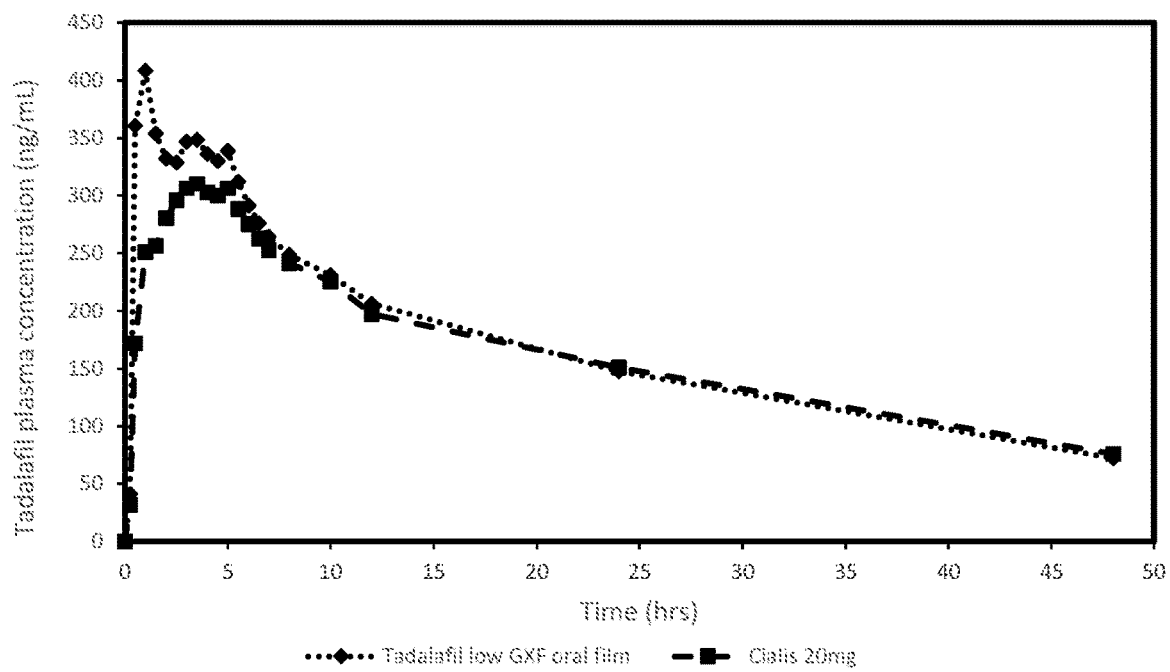
FIG. 1 graphically depicts in vivo absorption of tadalafil oral film formulation having a low content of HPC-GXF compared with the tadalafil brand tablet.

The oral film dosage form disclosed herein generally involves a film formulation comprising a very low quantity or percentage of highly viscous polymers to reduce the $C_{max}$ resulting from the early in vivo absorption of the API and potentially mitigating any side effects or adverse events generally associated with high early bioavailability.

An "oral film dosage form" generally refers to an edible composition that can be ingested by a subject (human or animal) to orally administer a predetermined amount of an active agent(s) to the subject, wherein the composition is in the form of a film.

The term "film" refers to a type of dosage form that is distinctly different from pills, tablets, caplets, and capsules, and in which the dosage form is a thin strip of material. Such films are typically rapidly disintegrating or rapidly dissolving, but can also exhibit longer disintegration time when required. The films are generally sufficiently flexible to allow bending or even folding without breaking. The films typically have length and width dimensions on the order of 5 to 35 mm, although larger or smaller dimensions are possible and may be desirable in particular circumstances, and a thickness on the order of 5 to 300 μm, although larger or smaller thicknesses are possible and may be desirable in certain circumstances.

The term "matrix" or "film matrix" refers to the polymer component or mixture of polymers, which creates the film forming matrix supporting the API within the oral film dosage form.

The term "active agent(s)" refers mainly to active pharmaceutical ingredients (API), but may also refer generally to any agent(s) that chemically interacts with the subject to which it is administered to cause a biological change, such as, but not limited to, eliminating symptoms of disease or regulating biological functions.

The term "amorphous" refers to the non-crystalline form of the solid, a state that lacks the regular crystalline organization of atoms. The amorphous content (amorphicity) of a solid can be accurately and precisely assessed using a number of well-established methodologies, including isothermal calorimetry, Powder X-ray Diffraction (PXRD), Differential Scanning calorimetry (DSC), Continuous Relative Humidity Perfusion, Microcalorimetry (cRHp), and Dynamic Vapor Sorption (DVS). In this document, the term amorphous also refers to an active agent(s) that exhibits 30% or more than 30% of amorphous material, more preferably above 50%.

The term "stable" refers to a product which exhibits no changes in the dissolution profile or remains within the established specifications and recovery when the product is exposed to normal stability conditions (e.g., 25° C./60% RH and 40° C./75% RH) for an extended period of time.

The term "non-solubilized" means that the majority of the amorphous or partially amorphous active agent(s) is uniformly distributed as solid particles into a polymer matrix (e.g., a continuous and homogenous semi-solid phase). The stability of an API can be increased in a finished film product by using the API as a partially/non-solubilized dispersion. A solubilized API, particularly a crystalline API, may recrystallize over time, during shelf life and storage, which may adversely affect the overall bioavailability of the product. The choice of a partially/non-solubilized API can also be used to control the dissolution behavior and release of API from a film dosage for systemic uptake within a patient. Uptake and absorption of API is governed by the drug solubility, thus controlling its crystallinity and particle size allows us to influence the bioavailability of the API within the human or animal body.

The mean particle size diameter (D50) equal or lower than 250 μm, refers to the size distribution of the solid particle uniformly distributed in the matrix film. The size can be small enough to avoid any roughness texture or unpleasant mouth feel experience when orally ingested.

The term "suspended" (and variations thereof) refers to a dispersion of solid material (e.g., particles or powder) in a bulk liquid medium, in which the solid material is not completely dissolved on a molecular level, and will eventually settle out of the liquid in the absence of agitation. In a suspension, the suspended material is not completely dissolved in the liquid.

A film layer is a sheet-like material having a thickness that is much less than its length or width. For example, oral transmucosal devices typically have a thickness on the order of about 50 μm to 500 μm (i.e., 0.05 mm to 0.5 mm), although thicker or thinner films may be suitable; and width and length dimensions typically on the order of about 5 mm to 36 mm, though larger or smaller dimensions can be used. The film layer could as well be round and oval in shape, and have straight or rounded corners.

The buccal or sublingual film dosage form can comprise a single film layer, or multiple layers. In some embodiments, a bilayer or multilayer film would include a mucoadhesive layer containing the API which is placed against the oral mucosa and a second layer directed outwards from the mucosa serving as a protective barrier against abrasion from the tongue or mastication. This protective layer also serves to favor the directed absorption of the API within the oral cavity rather than enteric uptake in the gastrointestinal (GI) tract. The term "mucoadhesive or bioadhesive" means that the composition of the film layer is formulated to adhere to the mucous membrane through which delivery of the active agent is targeted. For example, bioadhesive polymers used in formulating the film should be selected to exhibit adequate adhesion within the environment at the targeted mucous membrane to ensure that the bioadhesive layer remains in contact with the mucous membrane to which it is applied and allows the active agent to directly enter the blood stream through the mucous membrane.

The poor water solubility of the poorly water-soluble substance to be used for the solid preparation of the present disclosure means the property associated with difficulty of solubilizing the API in water. In the present disclosure, for example, the solubility of a poorly water-soluble substance at 37° C. is not more than 10 mg/L, preferably not more than 1 mg/L, more preferably not more than 0.5 mg/L.

An API or drug product is considered highly soluble when the highest dose strength is soluble in <250 ml water over a pH range of 1 to 7.5 as per the Biopharmaceutics Classification System (BCS).

As used herein, the solubility is determined as follows. First, an excess amount of a poorly water-soluble substance is added to purified water (5 ml). The obtained mixture is incubated in a thermostatic tank at 37° C. for 30 min, and stirred in a voltex mixer. The cycle of incubating and stirring is repeated 3 more times, and the obtained suspension is filtered through a syringe filter (manufactured by Japan Pall, trade name: Acrodisc LC25, PVDF, pore size 0.2 mm). The concentration (mg/L) of the poorly water-soluble substance in the filtrate is taken as the solubility.

According to certain embodiments, the oral film formulation comprises a film matrix and an API. The film matrix comprises a very low quantity or percentage of highly viscous polymers (less than about 5% by dry weight) to reduce the $C_{max}$ resulting from the early in vivo absorption of the amorphous API and potentially mitigating any side effects generally associated with such high early onsets when administering a film with an active agent or API which is poorly water soluble.

HPC, having a molecular weight range between 200,000 and about 500,000 Dalton, with a viscosity between 100 to approximately 500 cps (determined at 2% concentration in water by weight at 25° C. using a Brookfield LVF viscometer with spindle no. 2 at 60 rpm) was found to significantly reduce the $C_{max}$ related to in vivo absorption of certain poorly water soluble API, such as Tadalafil. As the oral film has a residence time in the mouth of less than 10 minutes, the oral film is effectively swallowed and enters into the GI tract, where the API absorption predominantly occurs. It was surprising and unexpected to see the HPC having an effect on the in vivo absorption and bioavailability of the API hours later down the GI tract. What was particularly unexpected was that a very low percentage (in the exemplary embodiment outlined herein as low as about 1.5% by dry weight) of HPC was highly effective in controlling the release of the API, and more particularly of mitigating the high $C_{max}$ typically associated with early onset of oral film administered APIs. A specific grade/MW of HPC, such as HPC-GXF, was found to act over a long time period possibly over hours, long after the film has been dissolved or disintegrated in the subject's oral cavity. Consequently, during clinical trials, the bioavailability of the API from different formulations was tested in patients. A first formulation (F1) having no HPC-GXF, a second formulation (F2) having a low concentration of HPC-GXF, and a third formulation (F3) having a very low concentration of HPC-GXF (see Tables 1-3). The absorption of the oral film formulations (F1, F2, and F3) was compared with the in vivo bioavailability of the brand tadalafil tablet product (Cialis® 20 mg).

TABLE 1

List of raw materials in Formulation F-1

| Item # | Description | Function | Wet (%) | Dry (%) | mg/film |
|---|---|---|---|---|---|
| A | Methanol | Solvent (will be removed during manufacturing) | 9.15 | — | — |
| B | Acetone | Solvent (will be removed during manufacturing) | 48.40 | — | — |
| 1 | Sucralose | Sweetener | 0.24 | 0.57 | 1.22 |
| 2 | Menthol | Flavoring agent | 0.16 | 0.38 | 0.82 |
| 3 | Polyethylene Glycol | Plasticizer | 7.85 | 18.49 | 40.05 |
| 4 | Monoammonium glycyrrhizinate | Sweetener | 0.08 | 0.19 | 0.41 |
| 7 | Povidone | Film former polymer | 24.84 | 58.52 | 126.73 |
| 8 | Hydroxypropyl cellulose LF | Film former polymer | 2.62 | 6.17 | 13.37 |
| 9 | Hydroxypropyl cellulose GXF | Absorption modulator | — | — | — |
| 10 | Hydroxypropyl cellulose -SSL, Nisso | Film former polymer | 2.62 | 6.17 | 13.37 |
| 11 | Blue dye | Color | 0.02 | 0.05 | 0.10 |
| 12 | Titanium dioxide | Opacifier | 0.10 | 0.24 | 0.51 |
| 13 | Tadalafil | Active | 3.92 | 9.23 | 20.00 |
| Total | | | 100.00 | 100.00 | 216.58 |

TABLE 2

List of raw materials in Formulation F-2

| Item # | Description | Function | Wet (%) | Dry (%) | mg/film |
|---|---|---|---|---|---|
| A | Methanol | Solvent (will be removed during manufacturing) | 8.34 | — | — |
| B | Acetone | Solvent (will be removed during manufacturing) | 50.31 | — | — |
| C | Purified Water | Solvent (will be removed during manufacturing) | 5.28 | — | — |
| 1 | Sucralose | Sweetener | 0.43 | 1.18 | 2.43 |
| 2 | Menthol | Flavoring agent | 0.20 | 0.55 | 1.12 |
| 3 | Polyethylene Glycol | Plasticizer | 8.11 | 22.47 | 46.17 |
| 4 | Monoammonium glycyrrhizinate | Sweetener | 0.13 | 0.36 | 0.75 |
| 6 | Povidone | Film former polymer | 18.35 | 50.85 | 104.49 |
| 7 | Hydroxypropyl cellulose LF | Film former polymer | 4.13 | 11.46 | 23.55 |
| 8 | Hydroxypropyl cellulose GXF | Absorption modulator | 1.21 | 3.37 | 6.92 |
| 9 | Hydroxypropyl cellulose -SSL, Nisso | Film former polymer | — | — | — |
| 10 | Blue dye | Color | 0.01 | 0.03 | 0.06 |
| 11 | Titanium dioxide | Opacifier | — | — | — |
| 12 | Tadalafil | Active | 3.51 | 9.73 | 20.00 |
| Total | | | 100 | 100 | 205.49 |

TABLE 3

List of raw materials in F-3

| Item # | Description | Function | Wet (%) | Dry (%) | mg/film |
|---|---|---|---|---|---|
| A | Methanol | Solvent (will be removed during manufacturing) | 16.95 | — | — |
| B | Acetone | Solvent (will be removed during manufacturing) | 55.09 | — | — |

TABLE 3-continued

List of raw materials in F-3

| Item # | Description | Function | Wet (%) | Dry (%) | mg/film |
|---|---|---|---|---|---|
| 1 | Sucralose | Sweetener | 0.18 | 0.64 | 1.17 |
| 2 | Menthol | Flavoring agent | 0.32 | 1.14 | 2.07 |
| 4 | Polyethylene Glycol | Plasticizer | 1.11 | 3.97 | 7.18 |
| 5 | Oleoyl Polyoxyglycerides | Liquid crystallization inhibitor | 5.67 | 20.27 | 36.68 |
| 6 | Monoammonium glycyrrhizinate | Sweetener | 0.16 | 0.57 | 1.04 |
| 7 | Povidone | Film former polymer | 12.27 | 43.88 | 79.42 |
| 8 | Hydroxypropyl cellulose LF | Film former polymer | 4.06 | 14.52 | 26.28 |
| 9 | Hydroxypropyl cellulose GXF | Absorption modulator | 0.40 | 1.43 | 2.59 |
| 10 | Hydroxypropyl cellulose -SSL, Nisso | Film former polymer | — | — | — |
| 11 | Titanium dioxide | Opacifier | 0.70 | 2.51 | 4.55 |
| 12 | Tadalafil | Active | 3.09 | 11.05 | 20.00 |
| Total | | | 100 | 100 | 180.98 |

Referring to FIG. 1 and Table 4, the absorption and pharmacokinetic data for F-1 is shown, compared with the same information as the brand name 20 mg tadalafil tablet (Cialis®). F-1 is an oral film with a film matrix containing no HPC-GXF and where the active ingredient is amorphous. The F-1 $C_{max}$ seen in the graph is substantially greater than the $C_{max}$ of the brand tadalafil tablet. F-1 is also not bioequivalent to the 20 mg brand tablet as the $C_{max}$ for F-1 substantially differs from that of the brand tablet. This exemplary data expose a major problem associated with the reformulation of an oral tablet API into an oral film API. The pharmacokinetics associated with oral film delivery differ substantially from that of the tablets. Accordingly, the F-1 is not a good candidate formula because of its important deviation from the brand $C_{max}$ which could be associated with increased side effects and adverse events arising from the peak in the API plasma concentration.

Figure 2:
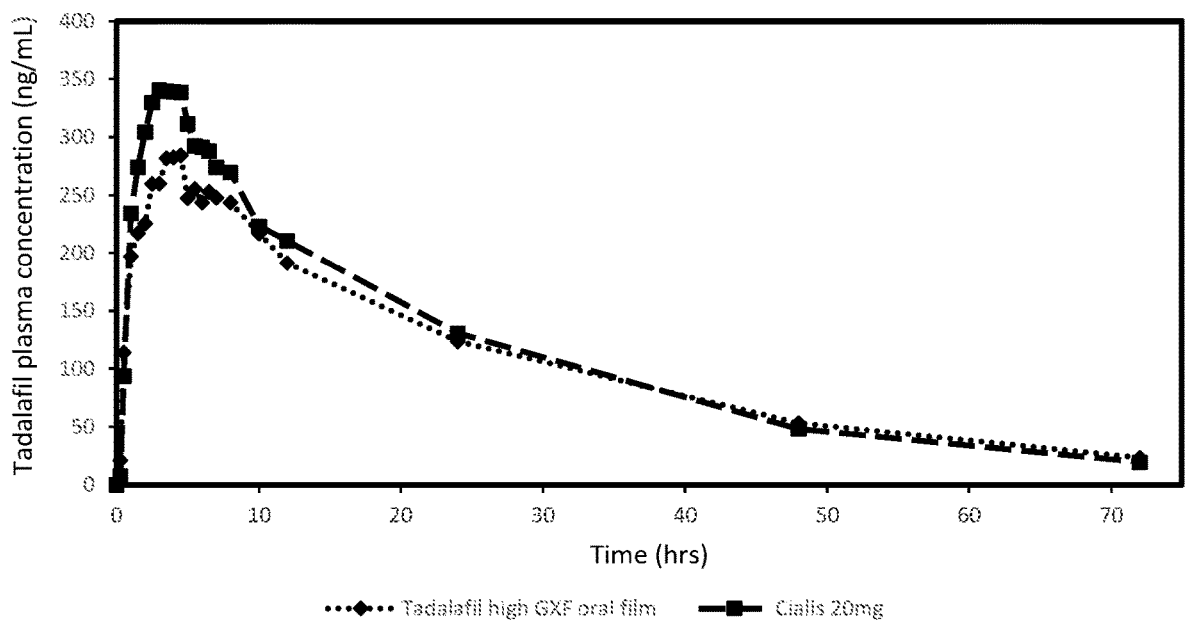
FIG. 2 graphically depicts in vivo absorption of tadalafil oral film formulation having a high content of HPC-GXF compared with the tadalafil brand tablet.

Referring to FIG. 2 and Table 5, the absorption and pharmacokinetic data for F-2 is shown compared with the same information for the 20 mg tadalafil brand tablet (Cialis®). F-2 is an oral film with a film matrix containing a low concentration of HPC-GXF, about 3.5% by dry weight. The F-2 data demonstrates a reduction of the $C_{max}$ when compared with the $C_{max}$ obtained from the F-1 and their respective deviation with regard to the reference 20 mg tadalafil brand tablet data. The addition of HPC-GXF to the formulation effectively reduced the $C_{max}$ to below the $C_{max}$ of the reference, thus reducing the likelihood of increased side effects associated with the API early $C_{max}$. It was surprising to observe the important effect on the $C_{max}$ obtained from the presence of a low concentration of HPC-GXF (about 3.5% by dry weight) in the film matrix. This demonstrates that addition of low quantities of high MW HPC effectively modulates the in vivo absorption of the API. The controlled absorption demonstrated with the HPC-GXF may also be applicable to other APIs with similar molecular characteristics. Since high MW HPC effectively modulates the in vivo absorption of API, it may be used to more effectively modulate the in vivo absorption of API having different half-lives. As such, API with shorter half-life will gain from the delayed and modulated in vivo absorption obtained from the presence of HPC-GXF in the film matrix. This exemplary data expose a surprising benefit observed from the use of low concentration of high MW HPC.

Figure 3:
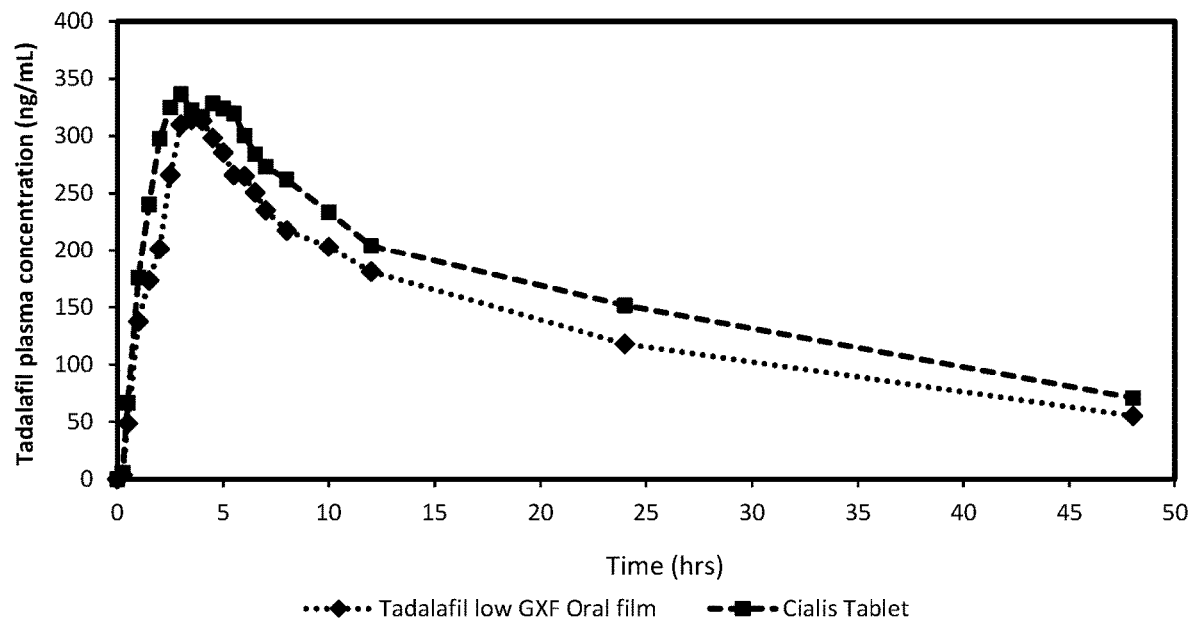
FIG. 3 graphically depicts in vivo absorption of tadalafil oral film formulation having low HPC-GXF compared with the tadalafil brand tablet.

Referring to FIG. 3 and Table 6, the absorption and pharmacokinetic data for F-3 is shown compared with the same information for the 20 mg tadalafil brand tablet (Cialis®). F-3 is an oral film with a film matrix containing a very low concentration of HPC about 1.5% by dry weight. The $C_{max}$ and AUC of F-3 now closely resemble the reference 20 mg tadalafil brand name tablet data. The F-3 (1.5% w/w HPC-GXF) data exhibits an intermediate $C_{max}$ value compared to F-1 (0% w/w HPC-GXF) and F-2 (3.5% w/w HPC-GXF). These experiments demonstrate that the addition of HPC-GXF to the formulation, even in very low concentrations, effectively slows enteric absorption and reduces the $C_{max}$ to below the $C_{max}$ of the reference product. Reducing the $C_{max}$ of an API administered via oral film dosage form reduces or at least partially mitigate the risks of side effects associated with the high $C_{max}$. In addition, the data indicates that F-3 appears bioequivalent to the 20 mg tadalafil brand tablet. HPC-GXF may thus be used for modulating in vivo absorption of API even several hours following administration and long after the film matrix has dissolved (see FIG. 3). The presence of low and very low concentrations (below 5% dry weight of HPC) effectively reduces the $C_{max}$ of tadalafil administered via an oral film dosage form.

What is most surprising is that a very low concentration, about 1.5% w/w HPC-GXF was found to affect the absorption of API long after being swallowed and entered the GI tract. HPC-GXF was shown to modulate the bioavailability (BA) of the API up to 40 hours after administration of the film (see FIG. 3). It was shown that approximately 1.5% by dry weight of the HPC-GXF was sufficient to reduce the $C_{max}$ for tadalafil below the comparative brand (Cialis® tablet 20 mg) tablet in vivo value. This allows the tadalafil oral film formulation to be considered bioequivalent with the brand name tadalafil tablet (Cialis® 20 mg). Our data clearly demonstrate that low and very low concentration (below 5% by dry weight) effectively lower the in vivo $C_{max}$ of very poorly water soluble APIs such as tadalafil and effectively potentially reduce the side effects generally known to be associated with early onset high $C_{max}$ peaks. This is of great significance in the absence of known mechanisms to effectively lower the $C_{max}$ of poorly water soluble API administered via oral film dosage forms.

TABLE 4

Pharmacokinetic data for plasma concentrations for formulation F-1

| Parameter | Intra-Subject C.V. (%) | Geometric LSmeans[a] Test | Geometric LSmeans[a] Reference | Ratio (%) | 90% Confidence Limits (%) Lower | 90% Confidence Limits (%) Upper |
|---|---|---|---|---|---|---|
| $C_{max}$ | 18.7 | 474.03 | 345.45 | 137.22 | 120.24 | 156.6 |
| $AUC_{0-T}$ | 10.2 | 7677.33 | 7382.7 | 103.99 | 96.52 | 112.04 |
| $AUC_{0-\infty}$ | 14.03 | 10321.66 | 10017.01 | 103.04 | 92.66 | 114.58 |

[a]units are ng/mL for $C_{max}$ and ng · h/mL for $AUC_{0-T}$ and $AUC_{0-\infty}$

TABLE 5

Pharmacokinetic data for plasma concentrations for Formulation F-2

| Parameter | Intra-Subject C.V. (%) | Geometric LSmeans[b] Test | Geometric LSmeans[b] Reference | Ratio (%) | 90% Confidence Limits (%) Lower | 90% Confidence Limits (%) Upper |
|---|---|---|---|---|---|---|
| $C_{max}$ | 14.7 | 310.27 | 366.97 | 84.55 | 75 | 95.32 |
| $AUC_{0-T}$ | 12.8 | 6841.35 | 17453.1 | 91.79 | 82.69 | 101.9 |
| $AUC_{0-\infty}$ | 15.87 | 10344.06 | 9652.34 | 107.17 | 94.17 | 121.96 |

[b]units are ng/mL for $C_{max}$ and ng · h/mL for $AUC_{0-T}$ and $AUC_{0-\infty}$

TABLE 6

Pharmacokinetic data for plasma concentrations for Formulation F-3

| Parameter | Intra-Subject C.V. (%) | Geometric LSmeans[c] Test | Geometric LSmeans[c] Reference | Ratio (%) | 90% Confidence Limits (%) Lower | 90% Confidence Limits (%) Upper |
|---|---|---|---|---|---|---|
| $C_{max}$ | 10.9 | 319.05 | 349.74 | 91.23 | 82.71 | 100.62 |
| $AUC_{0-T}$ | 11.3 | 6345.26 | 6595.28 | 96.21 | 86.97 | 106.42 |
| $AUC_{0-\infty}$ | 7.2 | 7718.06 | 7599.98 | 101.55 | 91.03 | 113.29 |

Figure 4:
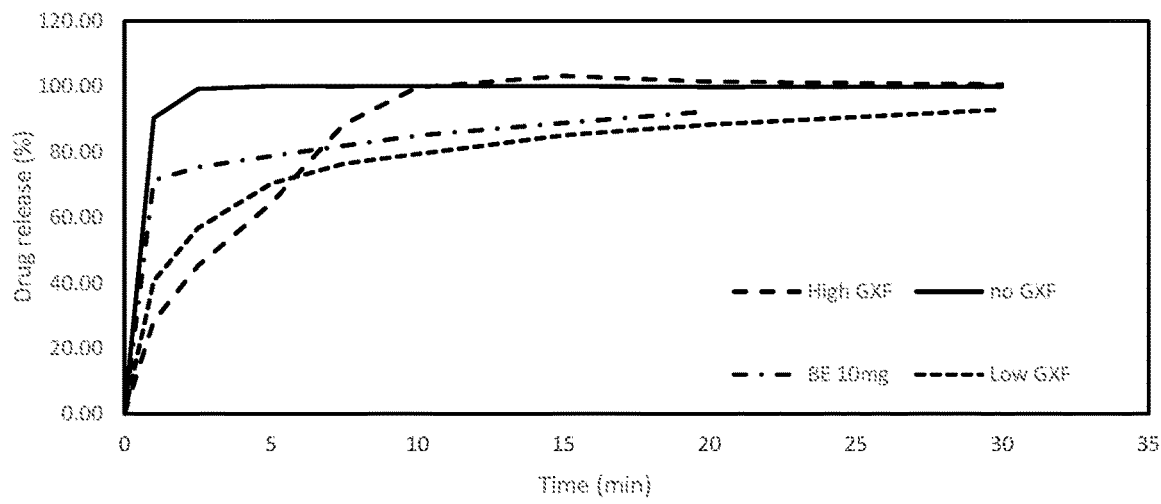
FIG. 4 graphically depicts dissolution of oral film formulations having various content of HPC-GXF.

[c]units are ng/mL for $C_{max}$ and ng · h/mL for $AUC_{0-T}$ and $AUC_{0-\infty}$ Referring to FIG. 4, the dissolution data profile for Formulations F-1, F-2, and F-3 (performed using paddles set at 50 rpm, with 1000 mL 0.5% w/v SLS, mesh 40) are shown. The dissolution data demonstrate starkly different dissolution profiles for F-1, F-2 and F-3. F-1 (the formulation without HPC) is shown to dissolve quickly with more than 90% of the film solubilized after 1 minute. The film shows almost total dissolution after the 2.5-minute mark with total dissolution after 5 minutes. The addition of low concentration (about 3.5% by dry weight) of HPC-GXF in F-2 significantly slows the dissolution of the film matrix in which less than 30% dissolved after one minute, less than 50% dissolved after the 2.5 minutes, and less than 90% of the film dissolved after 7.5 minutes. The dissolution of the low concentration HPC-GXF film (F-3) demonstrates a significant reduction in the dissolution rate in the first five minutes and increased dissolution following the first five minutes. The F-3 dissolution data surprisingly demonstrates that addition of very low concentration of HPC-GXF, about 1.5% by dry weight, also results in a much slower dissolution profile when compared with the dissolution data for F-1 (formulation without HPC-GXF). Even more surprisingly was the demonstration that about 1.5% by dry weight HPC-GXF yielded a very controlled progressive dissolution profile differing from both F-1 and F-2. F-3 demonstrates that very low concentrations of HPC-GXF can slow the dissolution of the film to over 20 minutes.

Referring back to FIGS. 3 and 4, very low concentrations of HPC-GXF in the oral film dosage appear to effectively modulate the in vivo absorption of the API even after the film matrix has completely dissolved.

TABLE 7

Dissolution data profile for Formulations F-1, F-2 and F-3, paddles set to 50 rpm, in 1000 mL of 0.5% w/v SLS, mesh 40, shown in FIG. 4.

| Time (Min) | F-1 | F-2 | F-3 |
|---|---|---|---|
| 0 | 0.00 | 0.00 | 0.00 |
| 1 | 90.38 | 28.45 | 40.70 |
| 2.5 | 99.13 | 45.26 | 56.79 |
| 5 | 100.05 | 64.37 | 70.35 |
| 7.5 | 99.97 | 88.39 | 76.37 |
| 10 | 100.10 | 99.63 | 79.30 |
| 15 | 100.00 | 103.19 | 85.02 |
| 20 | 99.72 | 101.48 | 88.34 |
| 30 | 99.96 | 100.55 | 92.83 |
| Infinity | 100.00 | 100.00 | 97.59 |

According to certain embodiments, the oral film dosage form film matrix comprises an in vivo absorption modulator having a viscosity of between 100-500 cps determined at 2% concentration in water by weight at 25° C. using a Brookfield LVF viscometer with spindle no. 2 at 60 rpm.

According to certain embodiments, the film matrix may also comprise pH modifiers, sweeteners, permeation enhancers, flavoring agents, plasticizers, film former polymers, opacifiers and solubilizers. The oral film may also comprise trace amounts of residual solvents. According to some embodiments, the flavoring agent may also act as a permeation enhancer.

According to certain embodiments, liquid film-forming formulations generally include at least one film-forming polymer and a solvent system. The solvent system can be comprised of a single solvent or a mixture of two or more solvents that are typically miscible. The liquid film-forming formulation may incorporate other ingredients that enhance or modify the functionality, processability, taste or aesthetics of the film. Such film-forming additives include colorants, opacifiers, flavorants, plasticizers, surfactants, etc.

Water soluble polymers that can be employed in the disclosed films include water soluble cellulose derivatives, including hydroxypropylmethyl cellulose, hydroxyethyl cellulose, hydroxypropyl cellulose, polyvinyl pyrrolidone, copovidone (a copolymer of 1-vinyl-2-pyrrolidone and vinyl acetate), other copolymers of vinyl pyrrolidone, other polymers or copolymers of substituted vinyl pyrrolidone, derivatives of polyvinyl pyrrolidone, polyethylene oxide (PEO), carboxymethyl cellulose, polyvinyl alcohol, polysaccharides, natural gums, including xanthan, tragacanth, guar, acacia and arabic gums, and water soluble polyacrylates. As well, practically water insoluble polymers, such as microcrystalline cellulose, ethyl cellulose, and hypromellose phthalate can be used in the formulation. Combinations of these water soluble and non-water soluble polymers or other polymers can also be used.

According to certain embodiments, the film matrix may also comprise various weight ratios of polymer/API. The polymer/API weight ratios may vary depending on the active agent. The polymer/API weight ratio is typically in the range of from about 2:1 to about 10:1 preferably in the range of about 3:1 to about 9:1 and more preferably in the range of about 4:1 to 8:1. In other words, the disclosed oral film dosage forms have a polymer component that is about 2 to about 10 times, preferably about 3 to about 9 times, and more preferably about 4 to about 8 times the weight of the API.

The content of the above-mentioned poor water solubility API in an oral film dosage form preparation is generally 1 wt % to 30 wt %, preferably 2 wt % to 25 wt %, more preferably 5 wt % to 15 wt %.

The content of the above-mentioned HPC having a molecular weight between about 200,000 and about 500,000 Daltons, as determined by size exclusion chromatography and a viscosity between about 100 to about 500 cps, as determined at 2% concentration in water by weight at 25° C. using a Brookfield LVF viscometer with spindle no. 2 at 60 rpm, in an oral film formulation is generally 0.25 wt % to 5.0 wt %, preferably 0.75 wt % to 3.5 wt %, more preferably 1.0 wt % to 2.0 wt %.

The disclosed oral film dosage form may have various weight ratios of high molecular weight polymer/active agent (HMWP/API). The HMWP/API weight ratios may vary depending on the active agent. The HMWP/API weight ratio is typically in the range of typically 2:1 to 12:1, preferably 5:1 to 10:1, and more preferably 6:1 to 8:1. In other words, the disclosed oral film dosage forms have an active agent that is about 2 to about 12 times, preferably about 5 to about 10 times, and more preferably about 6 to about 8 times the weight of the film matrix high molecular weight polymer.

According to certain embodiment, a 20 mg tadalafil oral film according to the present disclosure has a plasma $C_{max}$ of about 270 to 450 ng/mL, preferably about 300 to 410 ng/mL, more preferably 330 to 390 ng/mL.

According to certain embodiment, a 10 mg tadalafil oral film according to the present disclosure has a plasma $C_{max}$ of about 135 to 225 ng/mL, preferably about 150 to 210 ng/mL, more preferably 160 to 190 ng/mL.

According to certain embodiment, a 5 mg tadalafil oral film according to the present disclosure has a plasma $C_{max}$ of about 65 to 115 ng/mL, preferably about 75 to 105 ng/mL, more preferably 85 to 95 ng/mL.

According to certain embodiment, a 2.5 mg tadalafil oral film according to the present disclosure has a plasma $C_{max}$ of about 30 to 60 ng/mL, preferably about 35 to 55 ng/mL, more preferably 40 to 50 ng/mL.

According to certain embodiments, poorly water soluble APIs as outlined above are generally understood to be APIs categorized as a Class I or Class II of the BCS. The poorly soluble compound or API may also be a salt of the API.

Examples of drugs that could be beneficially employed in the disclosed processes include aceclofenac, adenosine, adriamycin, alfacalcidol, alosetron, alprazolam, amoxacilline, amphetamine sulfate, aripiprazole, aspirin, atorvastatin calcium, atropine, bacitracin, bicalutamide, bosentan, budesonide, buspirone, carbamazepine, celecoxib, cilostazol, cisapride, citalopram, clofazimine, clopidogrel bisulfate, cyclosporin, cyproterone acetate, delta-9-tetrahydrocannabinol, danazol, delavirdine, desloratadine, dexamethasone, diazepam, diclofenac, dipyridamole, docetaxel, dolargin, domperidine, domperidone, donepezil, doxorubicin, efavirez, entacapone, estazolam, everolimus, ezetimibe, felodipine, flunitrazepam, flutamide, folic acid, fulvestran, furosemide gefitinib, gliperizide, griseofulvin, hydrocortisone, ibuprofen, indomethacin, itraconazone, ketoconazole, ketoprofen, landoprazole, lenalidomide, levonorgestrel, loperamide, loratadine, lovastatin, lysozyme, mecamylamine, metaphetamine, morphine, naproxen, naproxone, nifedipine, nitrazepam, norethindrone, norgestimate, norgestrel, ofloxacin, olanzepine, omeprazol, paclitaxel phytosterol, pimozide, piroxicam, prazepam, progesterone, raloxifene HCl, raloxifene, ridogrel, salicylic acid, simvastatin, stigmasterol, tadalafil, temsirolimus, terfenadine, tolvaptam, tracolimus, triclabendazole, trypsinsulin, tubocurarine, zidovudine ziprazidone, and β-Estradiol.

According to certain embodiments, the oral film preparation having a high content of a poorly water-soluble API (e.g., oral film preparation wherein the content of a poorly water-soluble substance in the oral film preparation is not more than 20 wt %) is disclosed.

According to certain embodiments, the oral film dosage form comprises an API which is solubilized as opposed to being in particulate form within the film.

According to certain embodiments, the active agent or API may be dissolved in a highly viscous polymer. In such embodiments, the active agent or API is dissolved within the film matrix polymers during manufacture of the film. In addition, the API is believed to remain in an amorphous form once the film has dried, thus having a semi-solid film matrix, with the API either amorphous solubilized or crystalline dispersed within or a combination of both. Some films are taught using amorphous API dispersed within a film, however, some amorphous API are insufficiently stable and revert to their crystalline structure over time. The time at which those unstable amorphous form revert to their crystalline form will dictate if those recrystallizing API may suitably be used in oral film making under a dispersed solid within a polymer matrix. Recrystallization of the API or crystallization of the API dispersed within the film matrix is an ongoing stability concern that needs to be addressed to ensure film homogeneity over time. One way to address oral pharmaceutical film making with amorphous active that crystallize over a short period of time is to solubilize the active within the film matrix. Solubilizing the active during the manufacturing process overcomes shortcomings related to obtaining homogeneous or uniform content of API in the oral films. Homogeneity or content uniformity has been documented as a problem when manufacturing oral films with particulate actives, dissolving the active agent during the manufacturing process at least partially and in some cases substantially overcomes this shortcoming of oral film manufacturing processes. The solubilization of the API thus improves the content uniformity by improving the distribution of the active within the film blends prior to coating and drying of the film. Furthermore, some API under certain matrix compositions are able to remain in quasi or semi-solid form once the film has dried.

In such embodiments, in addition to improvement of content uniformity, the API stability may be improved by solubilization of API within the dried film. Moreover, solubilized API generally improves absorption and bioavailability of the API in the subjects' body following administration of the oral film, making the API more readily available. According to such an embodiment, the role of the high viscosity HPC-GXF grade is of significant importance since the readily bioavailable API may generate a high $C_{max}$. As detailed above, the addition of viscous HPC in low concentrations allows a certain modulation of the in vivo absorption and a reduction in the associated $C_{max}$.

Once the API is dissolved in the film in an amorphous state, the molecule has lost its crystalline structure and displays a low degree of order. The amorphous state is known to be more unstable and but generates significantly improved bioavailability. An amorphous API has a lower stability and may also have the tendency in short or long term to return to crystalline form, thereby changing the dissolution and absorption in vivo.

In general, solubilizing an API is desired to increase absorption by the human body in the GIT. For oral films, the API uptake may potentially occur through both buccal/ sublingual or enteral absorption. It is thus desirable to have an API which may be solubilized within the film making process and ultimately retains an amorphous structure within the final film product. API may also be categorized according to their level of permeation, (i.e. permeation through the GIT). A solubilized, amorphous API generally facilitates absorption and thus increases bioavailability. Although solubility and permeability are related to some extent, according to certain embodiments, the use of high viscosity HPC in low concentrations affects API absorption independent of their permeability. The HPC is believed to modulate absorption and thus bioavailability of API having either a high or a low permeation. However, the modulating effect of the HPC in low concentration will generally be affected by API solubility (also affected by particle size) for oral film having a dispersed particulate active therein (i.e. oral film where the API is found as a suspension as opposed to being dissolved in the film matrix during manufacture of the film).

According to certain embodiments, the oral film dosage form comprises an API which is placed in suspension within the film matrix. In such embodiments, the API is a particulate API which preferably has particles with a particle size of D(90) between about 2-20 μm. Practically insoluble or poorly water soluble API may be incorporated with an oral film dosage form as a particulate active.

According to certain embodiments, the oral film for providing transport of an agent in a buccal cavity of a subject comprises a dissolvable or disintegrable film matrix comprising hydroxypropylcellulose (HPC) and a particulate active agent having particle size D(90) between about 2-20 μm, wherein the HPC weight-average molecular weight determined by sized exclusion chromatography is between about 200,000 and about 500,000 Dalton and wherein the HPC has a viscosity of between about 100 to about 500 cps determined at 2% concentration in water by weight at 25° C. using a Brookfield LVF viscometer with spindle no. 2 at 60 rpm.

Figure 5:
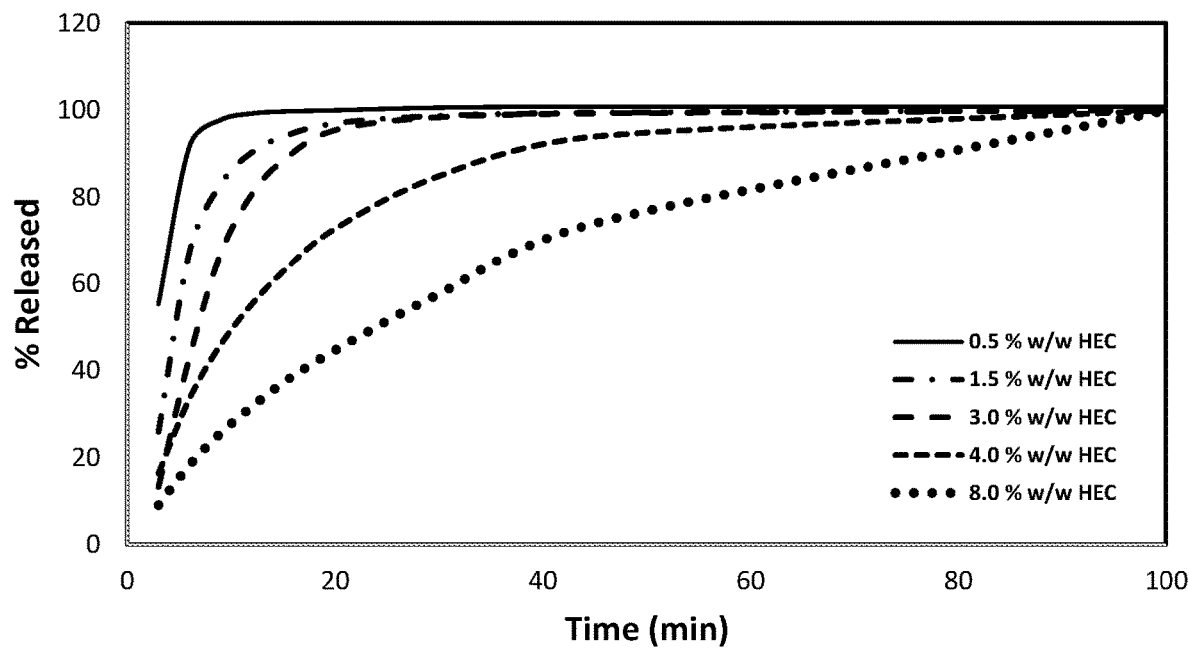
FIG. 5 graphically depicts dissolution profiles of Apomorphine with increasing HEC.
Figure 6:
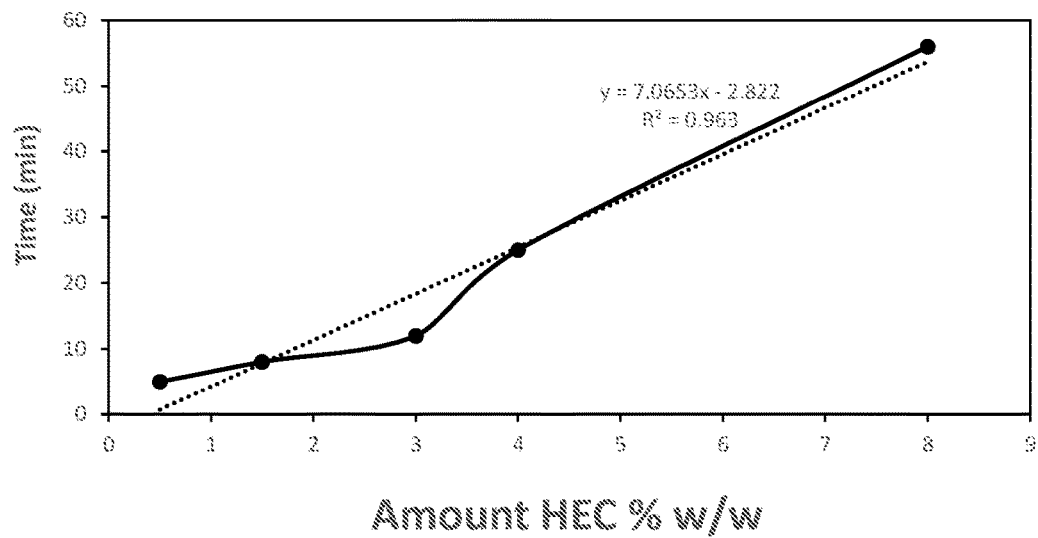
FIG. 6 graphically depicts 80% release (dissolution) vs amount of HEC in % w/w
Figure 7:
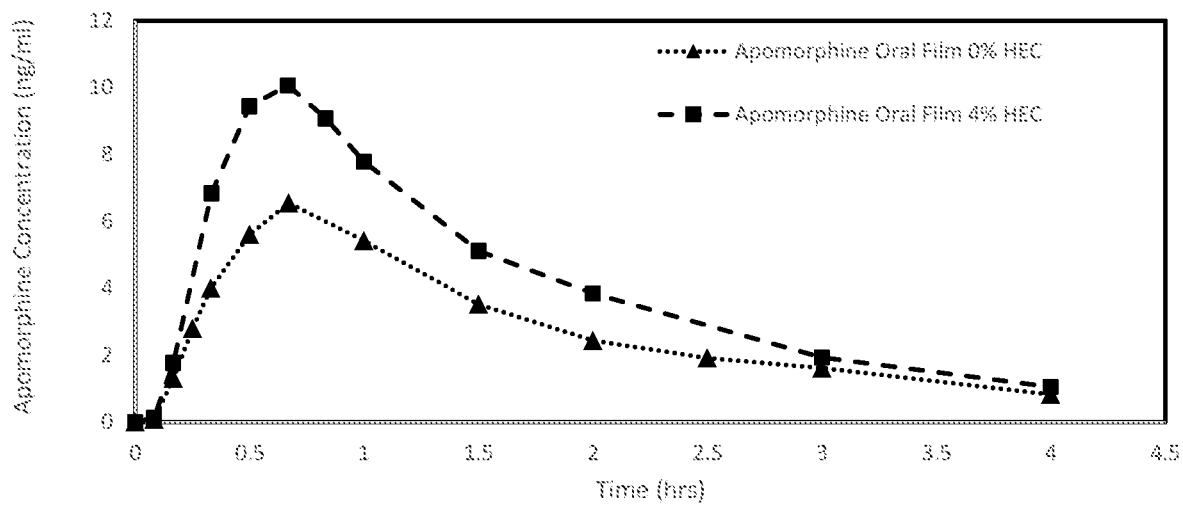
FIG. 7 graphically depicts clinical phase one data for Apomorphine.

According to certain embodiments, other high molecular weight film forming polymers, such as hydroxyethyl cellulose (HEC) (720,000 Daltons), can be used to control the release and bioavailability of an API (e.g., Apomorphine HCl). In these experiments, the formulation F-4 was kept constant in excipient composition, except for the HEC content, which was increased incrementally from 0.5% to 8.0% at a film thickness of about 0.15 mm. Film samples were prepared and assayed for drug release profiles using standard USP dissolution apparatus (see FIG. 5). The time to 80% released API can be used to compare the changes in dissolution with increasing HEC content (see Table 8). Surprisingly, it can be seen that using HEC in amounts ranging from 0.5 to 8.0% w/w we can effectively tune the release profile from 5 to 56 minutes with very fine precision. The 80% release unexpectedly yielded an almost perfectly linear relationship when plotting time versus the amount of HEC with a linear trend line of $R^2$=0.963 (see FIG. 6). Most significantly, this shows that with very small changes to the amount of HEC present we can readily control the release from an oral film for almost an hour. In this scenario, the film will strongly adhere to the oral mucosa via mucoadhesive polymers and then slowly disintegrate over time depending on the loading of high molecular weight polymer (e.g., HEC). During this experiment, several other polymers associated with control release strategies were assayed for functionality but did not generate positive results. These included ethylcellulose (EC, 75,000 Daltons) and hydroxypropyl cellulose (HPMC, 164,000 Daltons). These results were further correlated to in vivo results using a clinical phase of one study in healthy human subjects. This study involved using two oral film formulation prototypes; the first containing no (0%) HEC and the second containing 4% HEC. Following administration of the oral film, blood sampling was performed over a 24-hour period and analyzed for API accumulation. The bioavailability data can be seen in FIG. 7. Surprisingly we observed significant differences in the bioavailability of these two samples. Comparing the samples containing 0% and 4% HEC we see that the higher % HEC leads to about a 60% increase in the $C_{max}$ and a 40% increase in the AUC. These results suggest that not only can HEC be used to modulate the dissolution profile but can also be used to modulate the bioavailability of certain API.

The disclosed oral film dosage form comprising HEC may have various weight ratios of high MW polymer/active agent. The high MW polymer/active agent weight ratios may vary depending on the active agent. The high MW polymer/ active agent weight ratio is typically in the range of about 1:2 to about 1:50 preferably in the range of about 1:3 to about 1:45 and more preferably in the range of about 1:3 to about 1:10. In other words, the disclosed oral film dosage forms have an active agent that is about 2 to about 50 times, preferably about 3 to about 45 times, and more preferably about 3 to about 10 times the weight of the high MW polymer.

TABLE 8

HEC Content and Time to 80% w/w Released API

| HEC Content (% w/w) | Time to 80% released API (min.) |
|---|---|
| 0.5 | 5 |
| 1.5 | 8 |
| 3.0 | 12 |
| 4.0 | 25 |
| 8.0 | 56 |

Following administration of the oral film, blood sampling was performed over a 24-hour period and analyzed for API accumulation. The bioavailability data can be seen in Table 9.

TABLE 9

Summary of main study results of apomorphine formulation

| Parameter (Units) | Test A, 15 mg sublingual film, Clinical 1 | Test B, 15 mg sublingual film, Clinical 2 |
|---|---|---|
| Cmax (pg/mL) | 6828.3 | 11093 |
| $T_{max}$ (hours)[a] | 0.67 | 0.67 |
| $AUC_{0-T}$ (pg · h/mL) | 11226.5 | 16732 |
| $AUC_{0-\infty}$ (pg · h/mL) | 12486.8 | 18242 |
| $T_{half}$ (hours) | 1.24 | 1.06 |
| % High MW HEC | 0 | 4% |

TABLE 10

General formulation for apomorphine-HEC film

| Item # | Description | Function | Wet (%) | Dry (%) | mg/film |
|---|---|---|---|---|---|
| A | Methanol | Solvent (will be removed during manufacturing) | 0.59 | — | — |
| B | Water | Solvent (will be removed during manufacturing) | 64.33 | — | — |
| 1 | Menthol | Flavor | 1.94 | 5.54 | 3.62 |
| 2 | Glycerin | Plasticizer | 1.77 | 5.04 | 3.29 |
| 3 | Sorbitol | Plasticizer | 1.77 | 5.04 | 3.29 |
| 4 | PEG | Plasticizer | 0.35 | 1.01 | 0.66 |
| 5 | Sucralose | Flavour | 0.38 | 1.09 | 0.71 |
| 6 | Pullulan | Film former polymer | 11.78 | 33.59 | 21.94 |
| 7 | Klucel JF | Film former polymer | 0.88 | 2.52 | 1.65 |
| 8 | Xanthan gum | Film former polymer | 0.68 | 1.93 | 1.26 |
| 9 | Maltodextrin M180 | Disintegrant | 1.18 | 3.36 | 2.19 |
| 10 | Yellow Iron Oxide | Colorant | 0.44 | 1.26 | 0.82 |
| 11 | Purity 21 Starch | Matrix filler | 1.21 | 3.44 | 2.25 |
| 12 | Hydroxyethyl cellulose (HEC) Natrosol 250M | Control release film forming polymer | 1.07 | 3.06 | 1.28 |
| 13 | Apomorphine | API | 8.06 | 22.97 | 15.00 |
| Total | | | 100.00 | 100.00 | 64.59 |

In certain aspects of this disclosure, a process of making a product as disclosed includes a step of dispersing the active agent(s) in a dispersant/solubilizer to stabilize the amorphous form of the active agent(s) by inhibiting crystal nucleation and growth. A solid dispersion powder, comprising the active agent(s) in an amorphous form and a polymer dispersant, can be produced using known techniques. Examples of polymers that can be used as dispersants include cellulose acetate, cellulose acetate phthalate, copovidone, polyvinylpyrrolidone, ethylcellulose, eudragit E, eudragit NE, eudragit L & S, eudragit RL & RS, hydroxypropyl cellulose, hydroxyethylcellulose, hypromellose, hypromellose phthalate, hypromellose succinyl acetate, ethylene glycol, propylene glycol block copolymers (polaxamer), polyethylene glycol, polymethacrylates, polyvinyl acetate phthalate, polyvinyl caprolactam-polyvinyl acetate-polyethylene glycol graft copolymer and povidone.

The amorphous active agent(s) or solid dispersion containing the amorphous active agent(s) is mixed with the liquid film-forming formulation without dissolving the active agent(s). The suspension is mixed at a certain speed and for a limited time to produce a blend that has a uniformity of content of the suspended active agent(s), an acceptable low level of air bubbles, while maintaining the amorphous nature of the active agent(s). In addition, to increase the stability of the produced film, dispersants with known stability-enhancing effects by recrystallization prevention can be used. Stability of the oral film includes stability against the formation of degradation products over a defined period of time, as well as maintained amorphicity and resistance to heat. The stability of the oral film can be assessed by the dissolution profile of the active agent(s). Any decrease in the rate of dissolution is an indicator of amorphicity change of the active agent(s) within the film product.

The mixing speed in the wet blend is sufficient to introduce the amorphous or partially amorphous active agent(s) and create a wet blend suspension and final film product with uniformity of content as per definition in the United States Pharmacopeia (USP) test 905. The mixing time is the time required in combination with the mixing speed to create a uniform suspended mixture that does not solubilize the active agent(s). If the amorphous active agent(s) dissolves in the liquid blend, the physical and chemical characteristics of the final product would change significantly, render the process unstable and unpredictable, and increase the chance of potential recrystallization. The wet blend mixing and its composition must be set in a way to prevent re-agglomeration of the amorphous active agent(s).

According to an aspect of the disclosure, the total addition of highly viscous polymer HPC should not be more than about 5%. Film formulation comprising more than about 5% HPC will not yield an acceptable oral film dosage form.

Polycarbophil, HPMC, polyvinylpyrrolidone, polyethylene oxide, polyvinyl acetate or any acceptable pharmaceutical polymers capable of generating a viscosity between 100-500 cps at a concentration of 2% by weight in water The method and process of making the oral film dosage form disclosed herein generally involves, preparing, obtaining, or otherwise providing an active agent(s) in solid amorphous form or partially amorphous form, optionally combining the active agent(s) with a polymer dispersant to obtain an active agent(s) polymer-based particle system referred as a solid dispersion, uniformly suspending the amorphous active agent(s) in a liquid film-forming formulation, and removing solvents (such as by evaporation in a drying oven) to obtain a solid oral film dosage form that contains the amorphous or partially amorphous active agent(s) uniformly and stably distributed in a film matrix.

The disclosed dosage form will be illustrated by the following non-limiting Examples (see Tables 10 to 14).

TABLE 11

Exemplary formulation for Apomorphine-HEC film

| Item # | Description | Function | Wet (%) | Dry (%) | mg/film |
|---|---|---|---|---|---|
| A | Methanol | Solvent (will be removed during manufacturing) | 0.61 | — | — |

TABLE 11-continued

Exemplary formulation for Apomorphine-HEC film

| Item # | Description | Function | Wet (%) | Dry (%) | mg/film |
|---|---|---|---|---|---|
| B | Water | Solvent (will be removed during manufacturing) | 66.71 | — | — |
| 1 | Menthol | Flavor | 2.01 | 6.16 | 3.61 |
| 2 | Glycerin | Plasticizer | 1.84 | 5.62 | 3.29 |
| 3 | Sorbitol | Plasticizer | 1.84 | 5.62 | 3.29 |
| 4 | Polyethylene glycol | Plasticizer | 0.36 | 1.11 | 0.65 |
| 5 | Sucralose | Flavour | 0.39 | 1.21 | 0.71 |
| 6 | Pullulan | Film forming polymer | 12.22 | 37.38 | 21.92 |
| 7 | Klucel JF | Film forming polymer | 0.91 | 2.79 | 1.64 |
| 8 | Xanthan gum | Film forming polymer | 0.71 | 2.16 | 1.27 |
| 9 | Maltodextrin M180 | Disintegrant | 1.22 | 3.74 | 2.20 |
| 10 | Yellow Iron Oxide | Colorant | 0.46 | 1.40 | 0.82 |
| 11 | Purity 21 Starch | Matrix filler | 1.25 | 3.84 | 2.25 |
| 12 | Hydroxyethyl cellulose (HEC) Natrosol 250M | Control release polymer | 1.11 | 3.40 | 1.99 |
| 13 | Apomorphine | API | 8.36 | 25.58 | 15.00 |
| Total | | | 100 | 100 | 58.64 |

TABLE 12

Exemplary formulation for apomorphine-HEC film

| Item # | Description | Function | Wet (%) | Dry (%) | mg/film |
|---|---|---|---|---|---|
| A | Isopropanol | Solvent (will be removed during manufacturing) | 0.61 | — | — |
| B | Methyl ethyl ketone | Solvent (will be removed during manufacturing) | 70.36 | — | — |
| 1 | Glycerin | Plasticizer | 1.82 | 6.28 | 5.98 |
| 2 | Sucralose | Flavour | 0.39 | 1.35 | 1.28 |
| 3 | Ethyl cellulose (Ethocel) | Control release polymer | 14.68 | 50.57 | 48.16 |
| 4 | Hydroxypropylmethyl cellulose (HPMC E5) | Film forming polymer | 2.41 | 8.30 | 7.91 |
| 5 | Polyethylene glycol | Film forming polymer | 3.11 | 10.72 | 10.21 |
| 6 | Maltodextrin M180 | Disintegrant | 1.22 | 4.19 | 3.99 |
| 7 | Titanium Dioxide | Colorant | 0.82 | 2.84 | 2.70 |
| 8 | Apomorphine-HCl | API | 4.57 | 15.75 | 15.00 |
| Total | | | 100 | 100 | 95.24 |

TABLE 13

Exemplary formulation for Apomorphine-HEC film

| Item # | Description | Function | Wet (%) | Dry (%) | mg/film |
|---|---|---|---|---|---|
| A | Water | Solvent (will be removed during manufacturing) | 77.67 | — | — |
| 1 | Peppermin Oil | Flavor | 0.20 | 0.90 | 0.90 |
| 2 | Sorbitol | Plasticizer | 0.91 | 4.07 | 4.05 |
| 3 | Polyethylene glycol | Plasticizer | 0.20 | 0.90 | 0.90 |
| 4 | Sucralose | Flavour | 0.10 | 0.45 | 0.45 |
| 5 | Pullulan | Film forming polymer | 10.59 | 47.44 | 47.25 |
| 6 | MCT oil | Plasticizer | 3.03 | 13.55 | 13.50 |
| 7 | Locust bean gum | Viscosity modifier | 0.10 | 0.45 | 0.45 |
| 8 | Xanthan gum | Film forming polymer | 0.10 | 0.45 | 0.45 |
| 9 | Carrageenan | Viscosity modifier | 0.10 | 0.45 | 0.45 |
| 10 | Purity 21 Starch | Matrix filler | 1.01 | 4.52 | 4.50 |
| 11 | Hydroxyethyl cellulose (HEC) Natrosol 250M | Control release polymer | 1.11 | 4.97 | 4.95 |
| 12 | Polysorbate 80 | surfactant | 1.51 | 6.78 | 6.75 |
| 13 | Apomorphine-HCl | API | 3.36 | 15.06 | 15.00 |
| Total | | | 100 | 100.00 | 99.61 |

TABLE 14

Exemplary formulation for Apomorphine-HEC film

| Item # | Description | Function | Wet (%) | Dry (%) | mg/film |
|---|---|---|---|---|---|
| A | Ethanol | Solvent | 58.18 | — | — |
| B | Acetone | Solvent | 1.19 | — | — |
| 1 | Polyethylene Glycol | Film forming polymer | 16.10 | 39.65 | 39.65 |
| 2 | Sorbitol | Plasticizer | 2.28 | 5.62 | 5.62 |
| 3 | Hypromellose (HPMC E50) | Film forming polymer | 4.94 | 12.16 | 12.16 |
| 4 | Hypromellose (HPMC E5) | Film forming polymer | 9.78 | 24.07 | 24.07 |
| 5 | HPC GXF | Control release polymer | 0.50 | 1.22 | 1.22 |
| 6 | Ascorbic acid | Stabilizer | 0.24 | 0.59 | 0.59 |
| 7 | Sucralose | Flavor | 0.31 | 0.76 | 0.76 |
| 8 | Titanium dioxide | Colorant | 0.13 | 0.33 | 0.33 |
| 9 | Propylparaben | Stabilizer | 0.25 | 0.61 | 0.61 |
| 10 | Apomorphine | API | 6.09 | 15.00 | 15.00 |
|  | Total |  | 100.00 | 100.00 | 100.00 |

Using a rotary evaporator, olanzapine and sodium starch glycolate (1:1) are dissolved in acetone. Once fully dissolved, the solvent is removed at 40° C. under reduced pressure until a dry powder is obtained. The powder is collected from the flask and milled until D50 of 75 μm is obtained. This powder is then tested for active pharmaceutical agent(s) assay, particle size distribution, DSC and residual solvent concentration.

A polymer wet blend is created by adding PEO having 100,000 molecular mass and HPMC having a viscosity of about 50 cP (e.g., 40-60 cP), as measured with Ubbelohde viscometers at a 2% concentration in water at 20° C. (68° F.), (e.g., "Methocel E50") in a 4:1 mass-ratio pre-mixed together in water containing sucralose under stirring. The blend is mixed under vacuum for at least 3 hours or until a homogenous solution is obtained. The blend is degassed at low speed overnight.

The dry active powder and the wet blend are mixed together using low frequency mixing during a defined period of time and casted right away into a thin film layer. The film layer is dried using an oven with temperature set at a gradient of 30 to 95° C. The produced film sheet is then cut to specific size and individually packaged to provide an oral film configured as a single dosage form.

An oral dosage form comprised of amorphous tadalafil is prepared as outlined above and thereafter exposed to a temperature of 40° C. and a relative humidity of 75%. After an extended period of time (e.g., 6 months), it is determined that there is no or very little change in the dissolution profile (i.e., recovery to a deviation of less than 10% from the original dissolution profile) when the oral dosage form is returned to normal conditions (e.g., 25° C. and 60% relative humidity), indicating that the active agent has mostly (e.g., greater than 90%) remained amorphous. Deviation from the original dissolution profile refers to a maximum deviation in the amount of active agent dissolved at any particular time for a dosage form that is exposed to adverse conditions for an extended period of time as compared with a freshly prepared dosage form.

Manufacturing Procedure:

The oral film is produced by dissolving all the soluble ingredients in the media of choice and mixing until all excipients are solubilized yielding a uniform blend. The active ingredient is then added to the blend and solubilized or dispersed, depending on the formulation. The blend is mixed until uniform and then polymers are added to the blend and mixed until completely dissolved. Once dissolved and homogenous, the mixing speed is lowered to allow degassing of the blend.

Preparation of a film product typically involves casting or otherwise thinly spreading the liquid film formulation on a substrate, drying (e.g., evaporating) all or most of the solvent(s) from the film to produce a thin, semi-solid/solid film sheet of material, and cutting the film sheet into individual unit dosage forms for packaging or processing.

The above description is considered that of the preferred embodiment(s) only. Modifications of these embodiments will occur by those skilled in the art and by those who make or use the illustrated embodiments. Therefore, it is understood that the embodiment(s) described above are merely exemplary and not intended to limit the scope of this disclosure, which is defined by the following claims as interpreted according to the principles of patent law, including the doctrine of equivalents.

The invention claimed is:

1. An oral film dosage form designed for sublingual administration, the oral film dosage form comprising:
    a film layer comprising:
    an active agent contained in a polymer film matrix;
    wherein the film matrix comprises at least one disintegrant and hydroxypropyl cellulose in an amount of from 0.5 weight percent to 8.0 weight percent whereby the time to 80% release of the active agent is from about 5 minutes to about 20 minutes
    wherein the hydroxypropyl cellulose has a viscosity of from 150 cps to 400 cps determined at 2% concentration in water by weight at 25° C. using a Brookfield LVF viscometer with spindle no. 2 at 60 rpm, and
    wherein less than about 80% of the film is dissolved after 5 minutes when dissolution of the oral film is measured using paddles at 75 rpm in 1000 mL 0.5% w/v SLS, mesh 40.

2. The oral film of claim 1, configured to cause at least a portion of the active agent to be buccally absorbed upon administration to a subject.

3. The oral film of claim 1, wherein the film matrix comprises from about 0.5% by dry weight to about 3.5% by dry weight of hydroxypropyl cellulose.

4. The oral film of claim 1, wherein the film matrix comprises from about 1.0% by dry weight to about 2.0% by dry weight of the hydroxypropyl cellulose.

5. The oral film of claim 1, wherein the film matrix comprises about 1.5% by dry weight of the hydroxypropyl cellulose.

6. The oral film of claim 1, in which the active agent is selected from the group consisting of aceclofenac, adenosine, adriamycin, alfacalcidol, alosetron, alprazolam, amoxacilline, amphetamine sulfate, apomorphine, aripiprazole, aspirin, atorvastatin calcium, atropine, bacitracin, bicalutamide, bosentan, budesonide, buspirone, carbamazepine, celecoxib, cilostazol, cisapride, citalopram, clofazimine, clopidogrel bisulfate, cyclosporin, cyproterone acetate, delta-9-tetrahydrocannabinol, danazol, delavirdine, desloratadine, dexamethasone, diazepam, diclofenac, dipyridamole, docetaxel, dolargin, domperidine, domperidone, donepezil, doxorubicin, efavirez, entacapone, estazolam, everolimus, ezetimibe, felodipine, flunitrazepam, flutamide, folic acid, fulvestran, furosemide gefitinib, gliperizide, griseofulvin, hydrocortisone, ibuprofen, indomethacin, itraconazone, ketoconazole, ketoprofen, landoprazole, lenalidomide, levonorgestrel, loperamide, loratadine, lovastatin, lysozyme, mecamylamine, metaphetamine, morphine, naproxen, naproxone, nifedipine, nitrazepam, norethindrone, norgestimate, norgestrel, ofloxacin, olanzepine, omeprazol, paclitaxelb phytosterol, pimozide, piroxicam, prazepam, progesterone, raloxifene HCl, raloxifene, ridogrel, salicylic acid, simvastatin, stigmasterol, tadalafil, temsirolimus, terfenadine, tolvaptam, tracolimus, triclabendazole, trypsinsulin, tubocurarine, zidovudine ziprazidone, and 13-Estradiol.

7. The oral film of claim 1, wherein the hydroxypropyl cellulose/active agent weight ratio is in the range of about 1:2 to about 1:50.

8. The oral film of claim 1, wherein the hydroxypropyl cellulose/active agent weight ratio is in the range of about 1:3 to about 1:45.

9. The oral film of claim 1, wherein the hydroxypropyl cellulose/active agent weight ratio is in the range of about 1:3 to about 1:10.

10. The oral film of claim 1, wherein the weight of active agent is about 2 to about 50 times, the weight of the hydroxypropyl cellulose.

11. The oral film of claim 1, wherein the weight of active agent is about 3 to about 45 times, the weight of the hydroxypropyl cellulose.

12. The oral film of claim 1, wherein the weight of active agent is about 3 to about 10 times, the weight of the hydroxypropyl cellulose.

13. The oral film of claim 1, wherein the film matrix further comprises glycerin and menthol.

14. The oral film of claim 1, wherein the film matrix further comprises hydroxyethyl cellulose.

15. The oral film of claim 1, wherein the oral film dosage form further comprises from 1.0 percent to 5.0 percent by weight on a dry basis of a high molecular weight polymer having a viscosity of from 150 cps to 400 cps determined at 2% concentration in water by weight at 25° C. using a Brookfield LW viscometer with spindle no. 2 at 60 rpm.

16. The oral film of claim 1, wherein the film matrix comprises a total dry polymer content of from about 55% by dry weight to about 65% by dry weight.

17. The oral film of claim 1, wherein the film matrix comprises a total dry solubilizer content of from about 20% by dry weight to about 27% by dry weight.

18. The oral film of claim 1, wherein the disintegrant is maltodextrin.

19. The oral film of claim 1, wherein the active agent is present in an amount of about 1 wt % to about 30 wt %, based on total weight of the oral film dosage.

20. The oral film of claim 1, wherein the active agent is present in an amount of about 5 wt % to about 15 wt %, based on total weight of the oral film dosage.

* * * * *